United States Patent
Saadeh et al.

(10) Patent No.: US 10,660,891 B2
(45) Date of Patent: May 26, 2020

(54) PYRIMETHAMINE-BASED PHARMACEUTICAL COMPOSITIONS AND METHODS FOR FABRICATING THEREOF

(71) Applicant: Harrow IP, LLC, Nashville, TN (US)

(72) Inventors: Dennis Elias Saadeh, Irvine, CA (US); Annette Marleau, San Diego, CA (US); Thomas Ichim, San Diego, CA (US)

(73) Assignee: Harrow IP, LLC, Nashville, TN (US)

( * ) Notice: Subject to any disclaimer, the term of this patent is extended or adjusted under 35 U.S.C. 154(b) by 0 days.

(21) Appl. No.: 16/433,679

(22) Filed: Jun. 6, 2019

(65) Prior Publication Data

US 2019/0374540 A1     Dec. 12, 2019

Related U.S. Application Data

(60) Provisional application No. 62/682,632, filed on Jun. 8, 2018.

(51) Int. Cl.

| | | |
|---|---|---|
| *A61K 31/517* | (2006.01) | |
| *A61K 31/505* | (2006.01) | |
| *A61K 31/444* | (2006.01) | |
| *A61K 47/22* | (2006.01) | |
| *A61K 47/14* | (2017.01) | |
| *A61K 47/26* | (2006.01) | |
| *A61K 47/12* | (2006.01) | |
| *A61K 47/32* | (2006.01) | |
| *A61K 47/44* | (2017.01) | |

(52) U.S. Cl.
CPC ............ *A61K 31/505* (2013.01); *A61K 47/12* (2013.01); *A61K 47/14* (2013.01); *A61K 47/22* (2013.01); *A61K 47/26* (2013.01); *A61K 47/32* (2013.01); *A61K 47/44* (2013.01)

(58) Field of Classification Search
CPC ... A61K 31/517; A61K 31/505; A61K 31/444
USPC ...................................... 514/266.1, 272, 332
See application file for complete search history.

(56) References Cited

U.S. PATENT DOCUMENTS

| | | |
|---|---|---|
| 6,096,338 A | 8/2000 | Lacy et al. |
| 7,704,502 B2 | 4/2010 | Zhou et al. |
| 2011/0144043 A1 | 6/2011 | Frank |
| 2013/0045200 A1 | 2/2013 | Irving et al. |
| 2014/0234410 A1 | 8/2014 | Moodley et al. |
| 2015/0273033 A1 | 10/2015 | Bosch et al. |

OTHER PUBLICATIONS

PCT/US2019/035808 International Search Report and Written Opinion dated Sep. 30, 2019.
Khan et al. "The STAT3 inhibitor pyrimethamine displays anti-cancer and immune stimulatory effects in murine models of breast cancer," Cancer Immunol Immunother, Jan. 2018, 67(1)13-23.
"Pyrimethamine," Wikipedia, Nov. 5, 2017, 1-9 [Retrieved from the Internet: URL: https://en.wikipedia.org/w/index.php?title=Pyrimethamine&oldid=808836842 [retrieved on Aug. 1, 2019]].
"Polysorbate 80," Wikipedia, Sep. 26, 2017, 1-5 [Retrieved from the Internet: URL: https://en.wikipedia.org/w/index.php?title=Polysorbate_80&oldid=802498998 [retrieved on Aug. 1, 2019]].
"Polyethylene glycol," Wikipedia, Dec. 9, 2017, 1-4 [Retrieved from the Internet: URL: https://en.wikipedia.org/w/index.php?title=Polyethylene_glycol&oldid=814568876 [retrieved on Aug. 1, 2019]].
"Pyrimethamine," PubChem, Mar. 25, 2005, 1-3, 6 [Retrieved from the Internet: URL: https://pubchem.ncbi.nlm.nih.gov/compound/Pyrimethamine [retrieved on Aug. 1, 2019]].

*Primary Examiner* — Raymond J Henley, III
(74) *Attorney, Agent, or Firm* — Wagenknecht IP Law Group PC

(57) ABSTRACT

Pharmaceutical compositions that include aqueous suspensions of a therapeutically effective quantity of a diaminopyrimidine compound (such as pyrimethamine) are provided herein. Methods for fabricating the compositions and using them are also described.

27 Claims, No Drawings

PYRIMETHAMINE-BASED PHARMACEUTICAL COMPOSITIONS AND METHODS FOR FABRICATING THEREOF

CROSS REFERENCE TO RELATED APPLICATION(S)

This application claims the benefit of priority under 35 U.S.C. § 119(e) of U.S. Ser. No. 62/682,632, filed Jun. 8, 2018, the entire content of which is incorporated herein by reference.

FIELD OF THE INVENTION

The present invention relates generally to the field of pharmaceuticals and more specifically to pharmaceutical compositions that include as an active component a therapeutically effective quantity of a diaminopyrimidine compound (such as pyrimethamine), and to methods of preparing and using such compositions.

BACKGROUND

Pyrimethamine has been used for a long time to treat a variety of diseases and conditions such as, e.g., malaria. According to some theories, the health benefits attributable to pyrimethamine stem from it being a powerful inhibitor of the dihydrofolate reductase of plasmodia and other species, thereby blocking the biosynthesis of purines and pyrimidines, which are essential for DNA synthesis and cell multiplication.

In spite of a significant body of evidence in favor of using pyrimethamine, it has been determined that it may not work well in some cases. One serious drawback is the fact that there are instances where individuals, infants, children and adults who cannot swallow tablets, require a liquid form of the medication; however, pyrimethamine's solubility in water is poor.

It is, therefore, desirable to have pyrimethamine-based pharmaceutical compositions that are free from drawbacks and deficiencies, e.g., to have such compositions in a stable, liquid dosage form. This patent specification discloses such pharmaceutical compositions that can achieve such positive patient outcomes, and methods of fabricating and administering the same.

SUMMARY

According to one embodiment of the invention, a pharmaceutical composition formulated as a suspension is provided, the composition comprising a dispersed phase of particles comprised of a therapeutically effective quantity of at least one diaminopyrimidine compound, or derivatives or analogs thereof, and an anhydrous dispersion medium, and further including at least one pharmaceutically acceptable surfactant or solubilizing and suspending agent, and optionally, at least one derivative of folic acid, wherein the dispersed phase is dispersed within the dispersion medium.

According to various embodiments of the invention, the diaminopyrimidine compound may be any of pyrimethamine, trimetrexate, iclaprim, trimethoprim, 2,4-diaminopyrimidine, 4,5-diaminopyrimidine, piritrexim, or any combination thereof.

According to various embodiments of the invention, the derivative of folic acid that may be used is leucovorin.

According to various embodiments of the invention, the anhydrous dispersion medium comprises at least one of a vegetable oil (e.g., castor oil, soybean oil, coconut oil, avocado oil, olive oil, almond oil) and a medium chain triglyceride.

According to various embodiments of the invention, the pharmaceutically acceptable surfactant or solubilizing and suspending agent may be any of non-ionic polyoxyethlene-polyoxypropylene block copolymers, a water-soluble derivative of cellulose, optionally partially cross-linked polyacrylates, polyoxyethylene sorbitan monolaurates, polyoxyethylene sorbitan monopalmitates, polyoxyethylene sorbitan monostearates, polyoxyethylene sorbitan monooleates, glyceryl distearate, triglycerol monooleate, and combinations thereof.

According to various embodiments of the invention, the pharmaceutical compositions described herein may be orally administered to a mammalian subject in need of treatment for any of various diseases and/or maladies (e.g., toxoplasmosis, isosporiasis, cystoisosporiasis, actinomycosis, *Pneumocystis jirovecii* pneumonia, various myelodysplastic syndromes such as leukemia, and amyotrophic lateral sclerosis).

DETAILED DESCRIPTION

A. Terms and Definitions

Unless specific definitions are provided, the nomenclatures utilized in connection with, and the laboratory procedures and techniques of analytical chemistry, synthetic organic and inorganic chemistry described herein, are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, formulating compositions and testing them. The foregoing techniques and procedures can be generally performed according to conventional methods well known in the art.

It is to be understood that both the foregoing general description and the following detailed description are exemplary and explanatory only and are not restrictive of the invention claimed. As used herein, the use of the singular includes the plural unless specifically stated otherwise. The section headings used herein are for organizational purposes only and are not to be construed as limiting the subject matter described.

As used herein, "or" means "and/or" unless stated otherwise. Furthermore, use of the term "including" as well as other forms, such as "includes," and "included," is not limiting.

"About" as used herein means that a number referred to as "about" comprises the recited number plus or minus 1-10% of that recited number. For example, "about" 100 degrees can mean 95-105 degrees or as few as 99-101 degrees depending on the context. Whenever it appears herein, a numerical range such as "1 to 20" refers to each integer in the given range; i.e., meaning only 1, only 2, only 3, etc., up to and including only 20, as well as to the numbers in between such integers, e.g., 1.5, 2.5, and the like.

The term "pharmaceutical composition" is defined as a chemical or a biological compound or substance, or a mixture or combination of two or more such compounds or substances, intended for use in the medical diagnosis, cure, treatment, or prevention of disease or pathology.

The term "suspension" is defined for the purposes of the present application as a two-phase solid-in-liquid dispersion system having a first phase and a second phase. In other words, "suspension" is defined as a heterogeneous mixture in which the solute particles (i.e., those forming the solid phase) do not truly dissolve, but get suspended throughout the bulk of the solvent instead, without undergoing any significant precipitation within prolonged periods of time. It is further specifically provided that dispersion systems having three, four or more phases are not within the meaning of "suspension" for the purposes of the instant application.

Therefore, the above mentioned first phase of the suspension consists of a multitude of solid particles and is designated and defined as the dispersed phase, while the above mentioned second phase of the suspension is a liquid and is designated and defined as the dispersion medium, or, interchangeably and synonymously, the continuous phase.

Furthermore, the dispersed phase is dispersed in the dispersion medium, and the term "dispersed" is defined as meaning that the dispersed phase is statistically evenly distributed within the continuous phase throughout the entire volume of the suspension, with no statistically meaningful deviations in the concentrations of the dispersed phase in different portions of the suspension.

The term "stability" for the purposes of the present application refers to the ability of the dispersion to retain the pre-determined quantity of an active component (e.g., pyrimethamine) after the pre-determined period of storage time has expired. The storage may be at room temperature or at an elevated temperature, e.g., about 40° C.

A dispersion of this invention is defined as being "stable" if it still contains not less than about 90% and not more than about 110% of the original quantity of the active component (e.g., pyrimethamine) after each of the following periods of storage time: 30, 60, 90, and 150 days. If the quantity of the active component (e.g., pyrimethamine) is more than about 110% as measured by the UHPLC assay it is indicative of excessive undesirable flocculation of the particles of the dispersion. Such products are considered unacceptable. If the quantity is less than about 90% as measured by the same method it is indicative of excessive undesirable degradation of the active component (due to chemical destruction or any other cause), and such products are likewise considered unacceptable.

The term "medium-chain triglycerides" refers to triglycerides (i.e., tri-esters of glycerol and fatty acids) in which at least two of the three fatty acid moieties are derived from aliphatic (i.e., saturated open-chain) acids having between 6 and 12 carbon atoms; the fatty acids that are used for making medium-chain triglycerides are defined as medium-chain fatty acids and are caproic (IUPAC, hexanoic), enanthic (IUPAC, heptanoic), caprylic (IUPAC, octanoic), pelargonic (IUPAC, nonanoic), capric (IUPAC, decanoic), undecylic acid (IUPAC, undecanoic), or lauric (IUPAC, dodecanoic) acids.

The term "carrier" refers to a substance that serves as a vehicle for improving the efficiency of delivery and the effectiveness of a pharmaceutical composition.

The term "solubilizing agent" for the purposes of the instant application refers broadly to chemical compounds that improve the process of incorporating the solubilizate (i.e., active components described herein) into micelles; in other words the presence of a solubilizing agent makes the process of solubilization faster, easier, and/or more complete, as compared to compositions without it.

The term "suspending agent" is used herein interchangeably with the term "emulsifier" for the purposes of the instant application, and refers broadly to chemical compounds that help active pharmaceutical ingredients stay suspended in the formulation and prevents and/or reduces the phase separation of the two-phase dispersion systems described herein.

The term "therapeutically effective amount" is defined as the amount of the compound or pharmaceutical composition that will elicit the biological or medical response of a tissue, system, animal or human that is being sought by the researcher, medical doctor or other clinician.

The term "pharmaceutically acceptable" when used to defined a carrier, whether diluent or excipient, refers to a substance that is compatible with the other ingredients of the formulation and not deleterious to the recipient thereof.

The terms "administration of a composition" or "administering a composition" are defined to include an act of providing a compound of the invention or pharmaceutical composition to the subject in need of treatment.

B. Embodiments of the Invention

According to embodiments of the present invention, pharmaceutical compositions intended to prevent and/or treat various diseases and maladies, such as toxoplasmosis, malaria, isosporiasis, cystoisosporiasis, actinomycosis, *Pneumocystis jirovecii* pneumonia, leukemia, or amyotrophic lateral sclerosis, are provided. The pharmaceutical compositions of the instant invention are free of sulfonamide.

In various embodiments, the compositions of the invention may be provided in the form of a suspension. The suspensions include, consist of, or consist essentially of, an anhydrous dispersion medium (i.e., the continuous phase), a dispersed phase that is dispersed within the dispersion medium, and a pharmaceutically acceptable carrier. The dispersed phase includes, consists of, or consists essentially of, particles of a therapeutically effective quantity of at least one diaminopyrimidine compound (i.e., an active component), or derivatives or analogs thereof, and optionally may further include at least one derivative of folic acid, if desired. The dispersion medium includes at least one of a vegetable oil or a medium chain triglyceride, and further comprises at least one emulsifier or solubilizing and suspending agent.

Specific examples of acceptable diaminopyrimidine compounds that may be used according to the embodiments of the invention include, without limitation, pyrimethamine (also known under the trade name DARAPRIM®, Glaxosmithkline LLC, Wilmington, Del.), trimetrexate, iclaprim, trimethoprim, 2,4-diaminopyrimidine, 4,5-diaminopyrimidine, and piritrexim. These compounds are also listed in Table 1, below, including their respective chemical IUPAC names and structures:

TABLE 1

Diaminopyrimidine Compounds

| Compound | IUPAC Name | Chemical Structure |
|---|---|---|
| Pyrimethamine | 5-(4-chlorophenyl)-6-ethyl-pyrimidine-2,4-diamine | 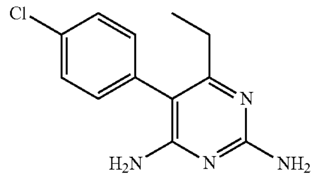 [SMILES: CCc1nc(N)nc(N)c1-c1ccc(Cl)cc1] |
| Trimetrexate | 5-methyl-6-[(3,4,5-trimethoxyphenyl) aminomethyl] quinazoline-2,4-diamine | 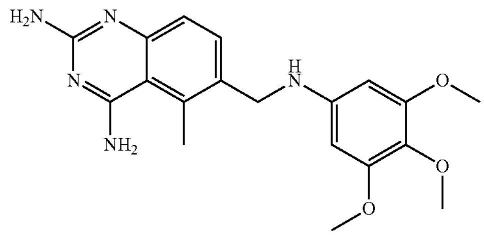 [SMILES: COc1cc(NCc2ccc3nc(N)nc(N)c3c2C)cc(OC)c1OC] |
| Iclaprim | 5-[(2-cyclopropyl-7,8-dimethoxy-2H-chromen-5-yl) methyl] pyrimidine-2,4-diamine | 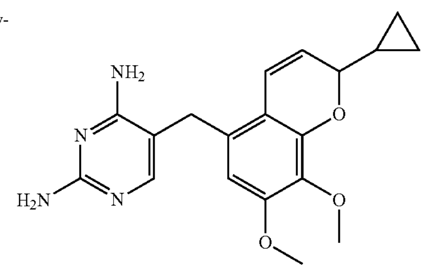 |
| Trimethoprim | 5-(3,4,5-trimethoxybenzyl)pyrimidine-2,4-diamine | 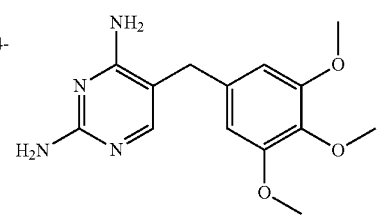 |
| 2,4-diaminopyrimidine | Pyrimidine-2,4-diamine | 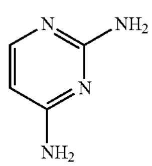 |
| 4,5-diaminopyrimidine | Pyrimidine-4,5-diamine | 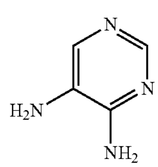 |
| Piritrexim | 6-[(2,5-dimethoxyphenyl)methyl]-5-methylpyrido[2,3-d]pyrimidine-2,4-diamine | 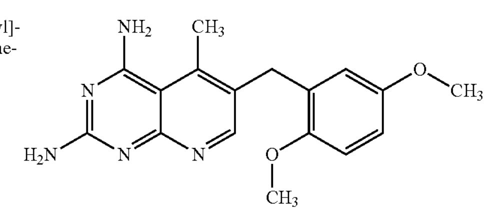 |

Those having ordinary skill in the art may use (an)other diaminopyrimidine(s) instead of, or in combination with, the above-named diaminopyrimidine-based compound(s), if desired.

The mass concentration of pyrimethamine and/or (an)other diaminopyrimidine-based compound(s) in the composition may be between about 0.1% and about 5.0%, such as between about 0.5% and about 2.0%, for example, about 0.5%, 1.0%, 1.5% or 2%, preferably about 1.0%.

If derivative(s) of folic acid is(are) present in the compositions of the instant invention, one specific example of such acceptable derivative is, without limitation, folinic acid (leucovorin, that is, 2-{[4-[(2-amino-5-formyl-4-oxo-5,6,7,8-tetrahydro-1H-pteridin-6-yl)methylamino]benzoyl]amino}pentanedioic acid, according to the IUPAC), which is an organic compound having the following chemical structure:

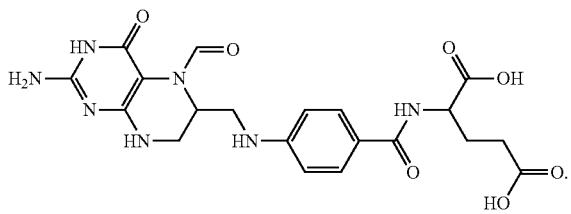 [SMILES: Nc1nc2c(c(=O)[nH]1)N(C=O)C(CNc1ccc(C(=O)NC(CCC(=O)O)C(=O)O)cc1)CN2]

Those having ordinary skill in the art may use (an)other derivative(s) of folic acid instead of, or in combination with, folinic acid, if desired. If derivative(s) of folic acid is(are) present in the compositions of the instant invention its(their) mass concentration in the composition may be between about 0.1% and about 5.0%, such as between about 0.5% and about 2.0%, for example, about 0.5%, 1.0%, 1.5% or 2%, preferably about 1.0%.

As mentioned above, the anhydrous dispersion medium of the composition of the present invention includes at least one vegetable oil or at least one medium chain triglyceride or a combination of products of both classes. The dispersion medium forms the major portion of the composition, its mass concentration in the composition being between about 80.0% and about 99.0%, such as between about 85.0% and about 95.0%, for example, about 85.0%, 85.5%, 90.0%, 90.5%, 91.0%, 91.5%, 92.0%, 92.5%, 93.0%, 93.5%, 94.0%, 94.5%, or 95.0%, preferably about 95.0%.

Specific examples of acceptable vegetable oils that may be used in the anhydrous dispersion medium according to various embodiments of the invention include, without limitation, castor oil, soybean oil, coconut oil, avocado oil, olive oil, almond oil, and combinations thereof. Partially hydrogenated oils can be also used, for example, polyoxyl 40 hydrogenated castor oil. Those having ordinary skill in the art may use (an)other vegetable oil(s) instead of, or in combination with, those mentioned above, if desired. Those having ordinary skill in the art will understand that all these oils represent complex blends of organic compounds, as opposed to individual organic molecules.

For example, castor oil is a complex mixture of several fatty acids, principally, ricinoleic acid, an unsaturated, 18-carbon fatty acid having a hydroxyl functional group on the $12^{th}$ carbon (IUPAC, 12-hydroxyoctadec-9-enoic acid). Those having ordinary skill in the art will understand that castor oil has a very complex chemical structure and is a mixture of triglycerides that varies, but commonly comprises ricinoleic acid (about 80%) plus triglycerides of linoleic (IUPAC, 9,12-octadecadienoic) and oleic (IUPAC, octadec-9-enoic) acids (about 20% combined).

Almond oil is another complex mixture of several fatty acids, which varies, but typically comprises 65 to 70 mass % of oleic, 20 to 25% of linoleic, up to 4% of palmitic (IUPAC, hexadecanoic) and small quantities of palmitoleic (IUPAC, hexadec-9-enoic) and stearic (IUPAC, octadecanoic) acids.

Coconut oil is yet another complex mixture of several fatty acids, which also varies, but commonly comprises about 45 to 50% of lauric acid, the balance being a combination of other medium-chain fatty acids described above, as well as palmitic and stearic acids.

Olive oil is yet another mixture of several fatty acids, which also varies, but its principal ingredient is oleic acid (about 75 to 85%), the balance being a combination of other fatty acids including linoleic and palmitic acids.

A variety of medium-chain triglycerides can be used for forming the anhydrous dispersion medium. For example, triglyceride(s) containing the aliphatic tails derived from caprylic acid or caproic acid may be so used. Those having ordinary skill in the art may use (an)other medium-chain triglyceride(s) instead of, or in combination with, those based on caprylic or caproic acids, if desired. One specific product comprising medium-chain triglycerides that may be used is UNISPEND® anhydrous sweetened liquid (Fagron, Inc., St. Paul, Minn.).

As stated above, the anhydrous dispersion medium used herein further comprises at least one emulsifier or solubilizing and suspending agent which may be present in the compositions of the instant invention at mass concentrations between about 0.1 mass % and about 10.0 mass %, such as between about 1.0 mass % and about 5.0 mass %, for example, about 1.0 mass %, 1.5 mass %, 2.0 mass %, 2.5 mass %, 3.0 mass %, 3.5 mass %, 4.0 mass %, 4.5 mass % or 5.0 mass %, preferably about 3.0 mass %.

Those having ordinary skill in the art will choose the most appropriate emulsifier or solubilizing and suspending agent. For example, one such emulsifier or solubilizing and suspending agent that may be used is a non-ionic polyoxyethlene-polyoxypropylene block copolymer having the following general structure:

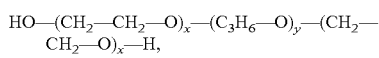

wherein in the chemical structure above x is an integer having the value of at least 8 and y is an integer having the value of at least 38. Polyoxyethlene-polyoxypropylene block copolymer(s) that can be used may be those belonging to the PLURONIC® or POLOXAMER® families, chemically, poly(ethylene glycol)-block-poly(propylene glycol)-block-poly(ethylene glycol), both available from BASF Corp. and from several other vendors and having the following general chemical structure:

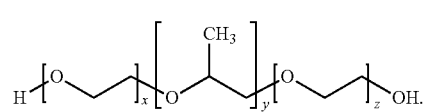

One more specific, but non-limiting example of a non-ionic polyoxyethlene-polyoxypropylene block copolymer that can be used is the product known under the trade name PLURONIC® L64, which is described by the chemical structure above, with the molecular weight of the polyoxypropylene portion of about 1,750 Daltons, about a 40% polyoxyethylene content (mass), and the average overall molecular weight of about 2,900 Daltons. Another specific non-limiting example of a non-ionic polyoxyethlene-polyoxypropylene block copolymer that can be used is the product known under the trade name Poloxamer 407° (also known as PLURONIC® F127), which is also described by the chemical structure above, with the molecular weight of the polyoxypropylene portion of about 4,000 Daltons, about a 70% polyoxyethylene content (mass), the overall molecular weight of between about 9,840 Daltons and about 14,600 Daltons.

Some non-limiting examples of other emulsifiers or solubilizing and suspending agents that may be used in combination with, or instead of, non-ionic polyoxyethlene-polyoxypropylene block copolymers, include derivatives of cellulose, optionally partially cross-linked polyacrylates, polyoxyethylene sorbitan monolaurates, polyoxyethylene sorbitan monopalmitates, polyoxyethylene sorbitan monostearates, polyoxyethylene sorbitan monooleates (e.g., members of POLYSORBATE® family of products), glyceryl distearate, triglycerol monooleate, and polysaccharide thickening agents such as xanthan gum.

For example, suitable derivatives of cellulose that may be used include, without limitations, carboxymethyl cellulose, methyl cellulose, hydroxyethyl cellulose, and hydroxypropyl cellulose (Dow Chemical, Midland, Mich.). Examples of acceptable partially cross-linked, polyacrylates that may be used include, without limitations, such as polymers of the CARBOPOL® family (Lubrizol, Wickliffe, Ohio). Typically, the cross-linking agents that may be used to cross-link such polyacrylates are allyl sucrose or allyl pentaerythritol.

Suitable products of the POLYSORBATE family (i.e., ethoxylated sorbitan esterified with fatty acids) that may be used include, without limitations, polyoxyethylene sorbitan monolaurates, polyoxyethylene sorbitan monopalmitates, polyoxyethylene sorbitan monostearates, or polyoxyethylene sorbitan monooleates, some of which are also known as TWEEN® products, such as POLYSORBATE® 80) (Croda, Wilmington, Del.).

One typical product of the latter family that can be used is Polysorbate 80 (chemically, polyoxyethylene (20) sorbitan monooleate, also known as sorbitan mono-9-octadecenoate poly(oxy-1,2-ethanediyl), i.e., a product of polycondensation of polyethoxylated sorbitan and oleic acid having 20 units derived from ethylene glycol), which is a nonionic surfactant and emulsifier.

Those having ordinary skill in the art will realize that yet (an)other additional emulsifier(s) or solubilizing and suspending agent(s) may be used if desired and will select such supplemental emulsifier(s) or solubilizing and suspending agent(s), as well as choose the quantity thereof.

According to various embodiments of the present application, the pharmaceutical compositions described herein are formulated as stable two-phase suspensions, as defined above. More specifically, according to these embodiments, the suspensions consist of two phases, i.e., the dispersed phase that is dispersed within the dispersion medium. The dispersed phase includes particles comprising a therapeutically effective quantity of the pharmaceutically active component, i.e., a diaminopyrimidine compound, or derivatives or analogs thereof. In some embodiments, no compounds other than the diaminopyrimidine compounds described hereinabove are present within the particles that form the dispersed phase. According to such embodiments, the dispersion medium is a liquid that includes all other compounds that are present in the pharmaceutical compositions described in the application. The application envisions no embodiment where a diaminopyrimidine compound can be used outside the dispersed phase, such as being a part of the dispersion medium.

In various embodiments, in addition to diaminopyrimidine compounds or derivatives or analogs thereof, the dispersed phase may optionally contain other compounds, such as, without limitation, stabilizers, antioxidants, preservatives, caking agents (e.g., colloidal silica dioxide), various flavoring agents or sweeteners.

According to various embodiments, methods for fabricating the above-described pharmaceutical compositions are also provided. A one-batch formulation method may be used, where the components of the pharmaceutical formulation can be combined in a single container; the components may be added to the container simultaneously or consecutively. Those having ordinary skill in the art can choose the best method for preparing the compositions.

Pharmaceutical compositions prepared as described above can be used to treat, prevent or alleviate toxoplasmosis, malaria, isosporiasis, cystoisosporiasis, actinomycosis, *Pneumocystis jirovecii* pneumonia, myelodysplastic syndromes (e.g., leukemia), and amyotrophic lateral sclerosis.

In further embodiments, pharmaceutical compositions prepared as described above can be used to enhance efficacy of one or more immune checkpoint inhibitors to improve effectiveness of such products when they are used for treating, e.g., cancer, as well as for any other purpose. In such treatments, pyrimethamine may be administered prior to, concurrent with, and subsequent to a checkpoint inhibitor.

More specifically, checkpoint inhibitors, the efficacy of which may be so improved, include, without limitations, those inhibitors that comprise one or more endpoints selected from tumor regression, tumor stabilization, reduction in tumor growth, inhibition of metastasis, stabilization of metastasis, reduction of metastatic growth, encapsulation of tumor and/or metastasis, augmentation of cytokines associated with tumor inhibition, decrease in cytokines associated with tumor progression, suppression of angiogenesis, augmentation of tumor infiltrating lymphocytes, switch of intratumoral macrophages from M2 to M1 phenotype, augmentation of tumor infiltrating dendritic cells, reduction of tumor associated T regulatory cells, and reduction in tumor associated myeloid suppressor cells.

Checkpoint inhibitors may include agents capable of suppressing expression or activity of such molecules as PD-1, PD-L1, CTLA-4, PD-L2, LAG3, Tim3, 2B4, A2aR, ID02, B7-H3, B7-H4, BTLA, CD2, CD20, CD27, CD28, CD30, CD33, CD40, CD52, CD70, CD112, CD137, CD160, CD226, CD276, DR3, OX-40, GALS, GITR, ICOS, HVEM, IDO1, KIR, LAIR, LIGHT, MARCO, PS, SLAM, TIGIT, VISTA, STAT3, or VTCN1. Exemplary checkpoint inhibitors include, but are not limited to, nivolumab, pembrolizumab, ipilimumab, tremelimumab, BMS-936559, durvalumab, atezolizumab, avelumab, MPDL3280A, MEDI4736, MSB0010718C, and MDX1105-01.

Pharmaceutical formulations described herein can be typically delivered orally. An ordinarily skilled physician may prescribe delivery by any other acceptable method if so desired and indicated; for instance, those having ordinary skill in the art may, if appropriate and medically indicated, alternatively choose such methods of delivery as intravenous, intramuscular, intratumoral injection, or parenterally or nasally.

It will be understood by those having ordinary skill in the art that the specific dose level and frequency of dosage for any particular patient may be varied and will depend upon a variety of factors including the activity of the specific compound employed, the metabolic stability and length of action of that compound, the age, body weight, general health, gender, diet of the subject being treated, and the severity of the particular disease or condition being treated. In one purely exemplary embodiment the dosage may be 25 mg to 100 mg once daily.

Accordingly, the invention also provides pharmaceutical kits. The kits include a sealed container approved for the storage of pharmaceutical compositions, the container containing one of the above-described pharmaceutical compositions. An instruction for the use of the composition and information about the composition are to be included in the kit.

The following examples are provided to further elucidate the advantages and features of the present invention, but are not intended to limit the scope of the invention. The examples are for the illustrative purposes only. USP pharmaceutical grade products were used in preparing the formulations described below.

C. Examples

Example 1. Preparing Pharmaceutical Composition #1

Pharmaceutical composition #1 was prepared as described below. The following products were used in the amounts specified:
(a) about 1.0 g of solid powdered pyrimethamine;
(b) about 0.1 g of solid powdered leucovorin calcium (1.08 g of leucovorin calcium is equivalent to 1.0 g of leucovorin);
(c) about 0.11 g of solid powdered xanthan gum;
(d) about 0.2 mL of POLYSORBATE® 80;
(e) about 100 mL of UNISPEND® anhydrous sweetened medium chain trigylceride;
(f) about 1.5 mL of artificial caramel flavor liquid; and
(g) a small quantity of glycerol sufficient to wet the powders as mentioned below.

Pyrimethamine, leucovorin calcium, and xantham gum were combined using mortar and pestle according to standard techniques of mixing solids, then the mixture was triturated to achieve uniformity. A small quantity of glycerol was added to wet the powdered mixture followed by trituration again to form a smooth paste.

The artificial caramel flavor liquid and POLYSORBATE® 80 were then added, with trituration followed by addition of the anhydrous sweetened medium chain trigylceride, and the product was transferred to a dispensing bottle. Finally, the mortar was washed using a small quantity of anhydrous sweetened medium chain trigylceride, and the wash was transferred to the bottle, to ensure the entire quantity of the active components has been so transferred, followed by packaging and labeling.

Example 2. Preparing Pharmaceutical Composition #2

Pharmaceutical composition #2 was prepared as described below. The following products were used in the amounts specified:
(a) about 4.0 g of solid powdered pyrimethamine;
(b) about 0.4 g of butylated hydroxytoluene;
(c) about 0.9 g of powdered sodium benzoate;
(d) about 0.4 g of solid powdered xanthan gum;
(e) about 4.0 g of POLYSORBATE® 80;
(f) about 6.0 mL of artificial caramel flavor liquid; and
(g) about 400 mL of caprylic/capric tryglycerides liquid.

Pyrimethamine, butylated hydroxytoluene, sodium benzoate, and xantham gum were combined using mortar and pestle according to standard techniques of mixing solids, then the mixture was triturated to achieve uniformity. A small quantity of glycerol was added to wet the powdered mixture, followed by trituration again to form a smooth paste.

The artificial caramel flavor liquid and POLYSORBATE® 80 were then added, with trituration followed by addition of the caprylic/capric tryglycerides, and the product was transferred to the dispensing bottle. Finally, the mortar was washed using a small quantity of caprylic/capric tryglycerides, and the wash was transferred to the bottle, to ensure the entire quantity of active components has been so transferred, followed by packaging and labeling.

Example 3. Preparing Pharmaceutical Composition #3

Pharmaceutical composition #3 was prepared. The same components in the same quantities were used as described in Example 2, above, except that caprylic/capric tryglycerides used in the composition of Example 2 was replaced by sweet almond oil in the same quantity of about 400 mL. The process of mixing the components for composition #3 was also the same as that described in Example 2.

Compositions #2 and #3 prepared as described above were then tested for stability chromatographically by high performance liquid chromatography (UHPLC). The results are shown in Table 2 below.

TABLE 2

Stability of Compositions of Examples 2 and 3

Quantity of Pyrimethamine Assayed, % of the Original Quantity, After a Period of Storage Time

| Composition | at room temperature | | | | | at 40° C. | | | | |
| --- | --- | --- | --- | --- | --- | --- | --- | --- | --- | --- |
| | Day 0 | Day 30 | Day 60 | Day 90 | Day 150 | Day 0 | Day 30 | Day 60 | Day 90 | Day 150 |
| From Example 2 | 106 | 106 | 102 | 108 | 108 | 105 | 104 | 101 | 108 | n/a |
| From Example 3 | 98 | 98 | 97 | 102 | 98 | 98 | 98 | 98 | 102 | n/a |

As can be seen from the results summarized in Table 2, the dispersions described in Example 2 (containing caprylic/capric tryglycerides liquid) and in Example 3 (containing sweet almond oil) possess sufficient stability at each point in time while being stored up to 150 days, at room temperature (~25° C.) and up to 90 days at 40° C.

Example 4. Preparing Pharmaceutical Composition #4

Pharmaceutical composition #4 was prepared as described below. The following products were used in the amounts specified:
(a) about 4.0 g of solid powdered pyrimethamine;
(b) about 0.4 g of butylated hydroxytoluene;
(c) about 8.0 g of colloidal micronized silicone dioxide ($SiO_2$);
(d) about 0.4 g of solid powdered xanthan gum;
(e) about 1.6 g of polyoxyl 40 hydrogenated castor oil;
(f) about 4.0 g of POLYSORBATE® 80;
(g) about 0.8 g of acesulfame potassium;
(h) about 6.0 mL of artificial caramel flavor liquid; and
(i) about 400 mL of caprylic/capric tryglycerides liquid.
Components (a)-(i) were mixed to yield composition #4. The process of mixing the components for the composition #4 was the same as that described in Example 2 (and $SiO_2$ was mixed together with the other solids).

Although the invention has been described with reference to the above examples, it will be understood that modifications and variations are encompassed within the spirit and scope of the invention. Accordingly, the invention is limited only by the following claims.

What is claimed is:

1. A pharmaceutical composition formulated as a suspension comprising:
   (a) a dispersed phase consisting of particles comprising a therapeutically effective quantity of at least one diaminopyrimidine compound, or derivatives or analogs thereof;
   (b) at least one pharmaceutically acceptable surfactant or solubilizing and suspending agent;
   (c) optionally, at least one derivative of folic acid; and
   (d) an anhydrous dispersion medium,
   wherein the dispersed phase is dispersed within the dispersion medium.

2. The pharmaceutical composition of claim 1, wherein the diaminopyrimidine compound is selected from the group consisting of pyrimethamine, trimetrexate, iclaprim, trimethoprim, 2,4-diaminopyrimidine, 4,5-diaminopyrimidine, piritrexim, and any combination thereof.

3. The pharmaceutical composition of claim 2, wherein the diaminopyrimidine compound is pyrimethamine.

4. The pharmaceutical composition of claim 1, wherein the derivative of folic acid is leucovorin.

5. The pharmaceutical composition of claim 1, wherein the anhydrous dispersion medium comprises at least one vegetable oil, at least one medium chain triglyceride, or any combination thereof.

6. The pharmaceutical composition of claim 5, wherein the at least one vegetable oil is selected from the group consisting of castor oil, soybean oil, coconut oil, avocado oil, olive oil, almond oil, and any combination thereof.

7. The pharmaceutical composition of claim 5, wherein the at least one medium chain triglyceride is a triglyceride having at least two fatty acid moieties that are derived from saturated open-chain fatty acids having between 6 and 12 carbon atoms.

8. The pharmaceutical composition of claim 7, wherein the saturated open-chain fatty acids are selected from the group consisting of caprylic acid and caproic acid.

9. The pharmaceutical composition of claim 1, wherein the pharmaceutically acceptable surfactant or solubilizing and suspending agent is selected from the group consisting of non-ionic polyoxyethlene-polyoxypropylene block copolymers, a water-soluble derivative of cellulose, optionally partially cross-linked polyacrylates, polyoxyethylene sorbitan monolaurates, glyceryl distearate, triglycerol monooleate, polyoxyethylene sorbitan monopalmitates, polyoxyethylene sorbitan monostearates, and polyoxyethylene sorbitan monooleates.

10. The pharmaceutical composition of claim 9, wherein the non-ionic polyoxyethlene-polyoxypropylene block copolymer is poly(ethylene glycol)-block-poly(propylene glycol)-block-poly(ethylene glycol).

11. The pharmaceutical composition of claim 9, wherein the water-soluble derivative of cellulose is selected from the group consisting of carboxymethyl cellulose, methyl cellulose, hydroxyethyl cellulose, and hydroxypropyl cellulose.

12. The pharmaceutical composition of claim 9, wherein the solubilizing and suspending agent is polyoxyethylene (20) sorbitan monooleate.

13. The pharmaceutical composition of claim 3, wherein the mass concentration of pyrimethamine in the composition is between about 0.1% and about 5.0%.

14. The pharmaceutical composition of claim 1, wherein the composition retains between about 90% and about 110% of the diaminopyrimidine compound after being stored at room temperature for each of 30, 60, 90 and 150 days, or after being stored at up to about 40° C. for each of 30, 60, and 90 days.

15. A method for treating or alleviating a disease, condition, syndrome, symptom, pathology, or malady in a mammalian subject in need of such treatment comprising oral administration to the subject the composition of claim 1, wherein the disease being treated is selected from the group consisting of toxoplasmosis, malaria, isosporiasis, cystoisosporiasis, actinomycosis, *Pneumocystis jirovecii* pneumonia, myelodysplastic syndromes, and amyotrophic lateral sclerosis.

16. A method of enhancing efficacy of an immune checkpoint inhibitor in a mammalian subject in need thereof, comprising administering to the subject the composition of claim 1 prior to, concurrent with, and subsequent to, administering the checkpoint inhibitor.

17. The method of claim 16, wherein the efficacy of the checkpoint inhibitor comprises one or more endpoints selected from the group consisting of tumor regression, tumor stabilization, reduction in tumor growth, inhibition of metastasis, stabilization of metastasis, reduction of metastatic growth, encapsulation of tumor and/or metastasis, augmentation of cytokines associated with tumor inhibition, decrease in cytokines associated with tumor progression, suppression of angiogenesis, augmentation of tumor infiltrating lymphocytes, switch of intratumoral macrophages from M2 to M1 phenotype, augmentation of tumor infiltrating dendritic cells, reduction of tumor associated T regulatory cells, and reduction in tumor associated myeloid suppressor cells.

18. The method of claim 16, wherein the checkpoint inhibitor is an agent capable of suppressing expression or activity of a molecule selected from a group consisting of PD-1, PD-L1, CTLA-4, PD-L2, LAG3, Tim3, 2B4, A2aR, IDO2, B7-H3, B7-H4, BTLA, CD2, CD20, CD27, CD28, CD30, CD33, CD40, CD52, CD70, CD112, CD137, CD160, CD226, CD276, DR3, OX-40, GALS, GITR, ICOS, HVEM, IDO1, KIR, LAIR, LIGHT, MARCO, PS, SLAM, TIGIT, VISTA, and VTCN1.

19. The method of claim 16, wherein the composition is administered at a concentration and frequency sufficient to inhibit activity of STAT3.

20. The method of claim 16, wherein the composition is administered as a liquid suspension.

21. The method of claim 16, wherein the composition is administered intravenously, intramuscularly, parenterally, nasally, intratumorally or orally.

22. The method of claim 16, wherein the checkpoint inhibitor is administered intravenously, intramuscularly, parenterally, nasally, intratumorally, or orally.

23. The method of claim 16, wherein the checkpoint inhibitor is an inhibitor of a checkpoint protein selected from the group consisting of PD-1, PD-L1, and CTLA-4.

24. The method of claim 23, wherein the inhibitor of PD-1 is an anti-PD-1 antibody selected from the group consisting of nivolumab and pembrolizumab.

25. The method of claim 23, wherein the inhibitor of PD-L1 is an anti-PD-L1 antibody selected from the group consisting of BMS-936559, durvalumab, atezolizumab, avelumab, MPDL3280A, MEDI4736, MSB0010718C, and MDX1105-01.

26. The method of claim 23, wherein the inhibitor of CTLA-4 is an anti-CTLA-4 antibody selected from the group consisting of ipilimumab and tremelimumab.

27. The method of claim 16, wherein the composition is administered at a dose and frequency sufficient to inhibit activity of STAT3.

* * * * *